US011957610B2

(12) United States Patent
Overdevest

(10) Patent No.: US 11,957,610 B2
(45) Date of Patent: Apr. 16, 2024

(54) POSITIONING DEVICE AND SYSTEM FORMED OF A POSITIONING DEVICE AND BASE BODY OF AN ORTHOPEDIC DEVICE

(71) Applicant: Otto Bock Healthcare Products GmbH, Vienna (AT)

(72) Inventor: Etienne Overdevest, Göttingen (DE)

(73) Assignee: OTTO BOCK HEALTHCARE PRODUCTS GMBH, Vienna (AT)

( * ) Notice: Subject to any disclaimer, the term of this patent is extended or adjusted under 35 U.S.C. 154(b) by 0 days.

(21) Appl. No.: 15/733,616

(22) PCT Filed: Mar. 15, 2019

(86) PCT No.: PCT/EP2019/056580
§ 371 (c)(1),
(2) Date: Sep. 16, 2020

(87) PCT Pub. No.: WO2019/179893
PCT Pub. Date: Sep. 26, 2019

(65) Prior Publication Data
US 2021/0169672 A1 Jun. 10, 2021

(30) Foreign Application Priority Data
Mar. 20, 2018 (DE) ..................... 10 2018 106 574.4

(51) Int. Cl.
*A61F 5/01* (2006.01)
(52) U.S. Cl.
CPC .... *A61F 5/0102* (2013.01); *A61F 2005/0158* (2013.01); *A61F 2005/0167* (2013.01); *A61F 2005/0181* (2013.01)

(58) Field of Classification Search
CPC .......... A61F 5/01; A61F 5/013; A61F 5/0102; A61F 5/0125; A61F 2005/0132;
(Continued)

(56) References Cited

U.S. PATENT DOCUMENTS 4,691,905 A 9/1987 Tamura et al.
5,788,618 A * 8/1998 Joutras ................. A63C 10/145
482/8
(Continued)

FOREIGN PATENT DOCUMENTS

AU 2359797 A 12/1997
DE 69434390 T2 4/2006
(Continued)

OTHER PUBLICATIONS

International Search Report for International Application No. PCT/EP2019/056580, dated Jul. 9, 2020, 12 pages.

*Primary Examiner* — Ophelia A Hawthorne
*Assistant Examiner* — Gina McCarthy
(74) *Attorney, Agent, or Firm* — HOLLAND & HART LLP

(57) ABSTRACT

A positioning device for arranging and orienting multiple securing elements on a base layer of a base body of an orthopaedic device. The positioning device includes a first holder having at least one receiving device for a securing element, and a second holder having at least one receiving device for a securing element, wherein the first holder and the second holder are mounted on one another such that they can swivel about a swivel axis about a restricted angular range starting from a starting position.

18 Claims, 19 Drawing Sheets

(58) Field of Classification Search
CPC ...... A61F 2005/0158; A61F 2005/0165; A61F 2005/0167; A61F 2005/0181; A61F 2/76; A61F 2/78; A61F 2/80; A61F 2/5046; A61F 2002/7868; A61F 2002/5047; A61F 2002/5055; A61F 2002/5056; A61F 5/0123; A61F 5/3753; B25B 27/00; B25B 27/14; F16B 37/044; F16B 37/045; F16B 37/046; F16B 39/101; B25C 1/005; A63C 10/145

See application file for complete search history.

(56) References Cited

U.S. PATENT DOCUMENTS

| | | | |
|---|---|---|---|
| 5,980,435 A | 11/1999 | Joutras et al. | |
| 2002/0183673 A1* | 12/2002 | Naft | A61F 5/0125 602/16 |
| 2003/0144620 A1* | 7/2003 | Sieller | A61F 5/0125 602/5 |
| 2004/0010213 A1* | 1/2004 | Gregory | A61F 5/3753 602/20 |
| 2014/0257157 A1* | 9/2014 | Zhong | A61F 5/01 602/6 |
| 2018/0243119 A1* | 8/2018 | Görnert | A61F 5/0123 |
| 2019/0076284 A1* | 3/2019 | Kwark | A61F 5/3753 |

FOREIGN PATENT DOCUMENTS

| | | |
|---|---|---|
| DE | 202007005891 U1 | 11/2007 |
| WO | 2008061300 A1 | 5/2008 |

* cited by examiner

POSITIONING DEVICE AND SYSTEM FORMED OF A POSITIONING DEVICE AND BASE BODY OF AN ORTHOPEDIC DEVICE

CROSS REFERENCE TO RELATED APPLICATIONS

This application is a U.S. National Entry and claims priority to PCT International Patent Application No. PCT/EP2019/056580, filed 15 Mar. 2019, and entitled "POSITIONING DEVICE AND SYSTEM FORMED OF A POSITIONING DEVICE AND BASE BODY OF AN ORTHOPAEDIC DEVICE", which claims priority to Germany Patent Application No. 10 2018 106 574.4 filed 20 Mar. 2018, the entire disclosures of which are incorporated herein by this reference.

TECHNICAL FIELD

The invention relates to a positioning device for arranging and orienting a plurality of fastening devices on a base layer of a main body of an orthopedic device, and to a system formed of a positioning device and of a main body of an orthopedic device. Orthoses or prostheses are considered in particular as the orthopedic device, although it is also possible in principle to use the positioning device in conjunction with other orthopedic devices, for example exoskeletons.

BACKGROUND

Orthosis or prosthesis components for receiving or for fastening to a body part are in particular prosthesis sockets, into which a stump of a limb is inserted, or orthosis shells or brackets, which are placed onto the body and fastened thereto in order to be connected, across a joint, to a second orthosis component via a joint device.

Prosthesis sockets are often produced from fiber-reinforced plastics which are placed onto supports, impregnated with resin and then cured. The supports can be designed as standard models or can be created on the basis of a cast of the respective stump. An anchor plate for securing a pyramid adapter or an adapter receptacle is cast in or fastened at a distal end of the prosthesis socket, such that the prosthesis socket can be connected to a distal joint device and to distal prosthesis components.

Orthosis components for receiving body parts or for fastening to body parts can be produced from plastic components. These components, which can be designed as shells or brackets or the like, can likewise be produced from fiber-reinforced plastic materials. The orthosis components can often be secured to the body part via fastening devices such as straps or buckles. By way of the fastening devices, the limb is enclosed and, if appropriate, the orthosis components are elastically deformed. Accordingly, the orthosis components can be elastically deformable to a limited extent.

In order to produce orthoses with orthosis components for bearing on and receiving body parts or limbs, joint devices together with the orthosis components are secured and laminated on a model of the limb, in the case of individually tailored orthoses. Alternatively, fastening elements for joint devices are held in an orientation relative to each other via fixing devices, so-called dummies or space holders, which have to remain in situ during the curing and production of the orthosis components.

SUMMARY

The object of the present invention is to make available a positioning device, for arranging and orienting a plurality of fastening devices on a base layer of an orthopedic device, and a system formed of a positioning device and of a main body, with which fastening devices for additional components can be positioned relative to each other within admissible parameters in order to permit individualization of the orthopedic device in a simple manner.

According to the invention, this object is achieved by a positioning device and by a system having the features disclosed herein. Advantageous embodiments and developments of the invention are disclosed the description and the figures.

In the positioning device according to the invention for arranging and orienting a plurality of fastening devices on a base layer of a main body of an orthopedic device, comprising a first holder having at least one receiving device for a fastening element, and a second holder having at least one receiving device for a fastening element, provision is made that the first holder and the second holder are mounted on each other so as to be pivotable about a pivot axis about a limited angle range proceeding from a starting position. By arranging the fastening elements on the holders that are mounted pivotably relative to each other, it is possible to modify the orientation and positioning of the fastening elements relative to each other on the respective holders, wherein the modification takes place within a pivoting range within which components can be fastened without difficulty to the orthopedic device via the fastening elements. For example, drives, guides, joints or dampers, which have only a limited angle tolerance, can thus be easily positioned on the base layer of the main body before the production thereof, such that, after the production of the orthopedic device or of the main body of the orthopedic device, no further intermediate pieces, tolerance-compensating means or adapters need to be provided in order to be able to secure the component to the respective fastening element. By way of the positioning device, the fastening elements are arranged on the base layer in the defined positions relative to each other, wherein the fastening elements can have a base from which at least one form-fit element protrudes. By way of the form-fit element, it is possible to secure further components to the main body, such as dampers, joint devices, drives, controls or the like. A form-fit element is also understood as a screw or a threaded rod. By arranging the fastening elements in the previously defined positions relative to each other, it is possible to choose from a pool of components with standardized connection devices, in order then to arrange them on the base layer and secure them to the main body. It is thus possible, for example, to adapt orthosis components individually to the respective patient or orthosis user and to arrange different actuators or joint devices or also correction devices on the orthosis components in order, for example, to adapt to progress in the recovery process or to react to changes in circumstances, for example to worsening disorders. In addition, the precision of the arrangement of the fastening elements on the main body is increased.

Each holder of the positioning device can have a plurality of receiving devices for in each case one fastening element, such that, for example, two or more fastening elements can be positioned in a defined allocation to each other on a distal component of the orthopedic device, and a plurality of fastening elements, for example three fastening elements, can likewise be oriented in a defined allocation to each other on the base layer of the main body on a proximal component of the orthopedic device. If a plurality of fastening elements are arranged on the orthosis components, the respective additional device such as actuator, damper or joint can be fastened in a rotationally rigid manner.

The receiving devices can have bearing surfaces for the respective fastening element, which bearing surfaces lie on a holder in a common plane. This ensures that all the fastening elements on a holder lie in a common plane or at a common level and can be tilted only together with the holder relative to the other holder and therefore to the arrangement plane of the other fastening elements. The configuration of bearing surfaces in one plane on a holder, for a uniform orientation of the fastening elements located thereon, facilitates standardization of the additional components such as joint devices, actuators or dampers, and also the production. It is also possible in principle to arrange all the fastening elements on a holder at different levels or in different planes, wherein the planes are preferably oriented parallel to each other, although they can also be tilted relative to each other. However, the arrangement in one plane facilitates both the production of the positioning device and the mounting of the fastening elements and of the structural parts to be secured thereon.

The receiving devices can be configured as sleeves, so as to be able to receive the fastening elements which, for example, have pegs, inner threads, shafts or similar from-fit elements or devices for securing the further components. The sleeves are preferably cylindrical, although other shapes, in particular oval or angular shapes, can also be provided in principle.

In a development of the invention, the holders are mounted pivotably on a central piece. This central piece serves for the independent pivoting of the holders relative to each other. It is thus possible to pivot one holder, for example a distal holder, independently of the other holder, a proximal holder, relative to the central piece. By way of the central piece, a basic orientation of the positioning device on the respective main body can be obtained, such that a relative movement of the holders with respect to the central piece and to each other about the pivot axis is possible within the respectively predefined, limited angle range. The pivot axis for the first and second holder is configured on the central piece. The holders can advantageously be fixed on the central piece once a position has been found. This can be done, for example, by clamping the holder on the central piece. The holders are preferably steplessly pivotable within the angle range and can be fixed on the central body in each position relative to each other and to the central body.

To be able to orient the positioning device on the main body and optionally secure it, a fixing device for orienting the whole positioning device on the main body can be arranged on the central piece. The fixing device can be a peg, a thread or another preferably form-fit or force-fit securing device. It is also possible in principle that the central piece and therefore the positioning device can be fixed on or at the main body via a force-fit fixing device, for example a magnet device or a combination of several magnet devices on the central piece.

In a development of the invention, the fixing device is configured such that the pivot axis of the two holders is oriented orthogonally with respect to a joint axis of a joint device that can be arranged on the main body. The joint device has a joint axis which aligns with the physiological joint axis and is correspondingly configured and oriented, in the best case coinciding with the physiological joint axis. The joint device is for example a prosthesis joint or an orthosis joint. If the pivot axis of the positioning device is coincident with the joint axis of the joint device, the pivotability of the holders relative to each other about the pivot axis permits individual customization to the respective main body or to a respective patient or to the respective device. For example, if the main body is an orthosis or a preliminary stage to an orthosis, the main body can be adapted to the individual body shape of the patient. If the base layer is arranged, for example, on a proximal and distal limb so as to span a joint, for example on the thigh and the lower leg of a patient, the different anatomical circumstances result in a large number of possible orientations of orthosis components proximally and distally from the natural joint axis. The longitudinal axis of the fixing device symbolizes or then corresponds to the joint axis of the joint device that is intended to be fastened later to the main body. The limited angle range on the positioning device about which the holders can be pivoted reflects the manufacturing tolerances or assembly tolerances of the joint devices, such that the assembly tolerances of the respective joint device can already be taken into consideration in the production of the main body.

An abutment element can be arranged on the central piece and, with a mating piece arranged on the respective holder, limits the angle range. The angle range about which the holders are pivotable about the pivot axis is thus adjustable or modifiable, for example to be able to take into consideration different assembly tolerances in the respectively provided component or the components. If angle-tolerant joint devices, actuators or dampers are used, the angle range chosen can be greater; if components are provided that are sensitive with respect to the tilting of the bearing points, the limited angle range can be made smaller and reduced to the respectively admissible extent.

The abutment element and/or the mating piece can be arranged adjustably on the central piece or the holder. An abutment element or a mating piece can be provided for each holder, such that an individual setting of the respective holder is possible by adjusting the abutment element or the mating piece. It is likewise possible that only one abutment element is provided, via which both holders are modifiable in terms of their adjustment range.

In a variant of the invention, provision is made that the abutment element is arranged on the central piece so as to be displaceable along the pivot axis and securable in the respectively desired position. By virtue of the displaceable arrangement of the abutment element along the pivot axis, it is possible, after arranging the central piece on the main body and optionally fixing it on the main body, to first of all position a holder and the fastening elements arranged thereon on the base layer of the main body. The holder is fixed in the position then found. The position of one holder limits the displacement path of the abutment element and defines the attainable maximum position of the abutment element with respect to the other holder. The remaining adjustment range or pivoting range of the other holder relative to the first holder is thus defined via the position of the abutment element on the central piece. When a setting of the holders for optimal orientation of the fastening elements on or at the main body is found within the maximum angle range, the holders are fixed on the central piece. The fastening elements are then secured on the base layer, for example by an adhesive, a filler compound, a compensating compound or via adapters. The positioning device thus affords the possibility or permitting an optimized arrangement of the fastening elements on the base layer, for example of a prosthesis or orthosis or of another orthopedic device, across a fixed tolerance range of the angle orientations of the fastening elements relative to each other. The maximum range of angle adjustment about the pivot axis is limited structurally. The abutment element produces a coupling between the holders, in such a way that the pivoting of one holder about a pivot angle is subtracted from the possible pivot angle of the other holder in the opposite direction. If, proceeding from the starting position, both holders have available a pivoting range of +−5° and if the first holder is pivoted upward about 3° in the case of a horizontal pivot axis, the other holder has available a pivoting range of 2° upward and 8° downward. With the positioning device arranged laterally on a support, this would mean, on the first holder, a pivoting in the lateral direction of 3°, which for the second holder would mean a maximum pivoting about 2° in the lateral direction or 8° in the medial direction.

If compensating measures have to be taken despite the pivoting of the holders within the maximum permissible angle range, for example because the allocation of an orthosis component for a thigh to an orthosis component for a lower leg does not permit a complete and optimized contact on the base layer, the free space is filled in, for example by an adhesive or a filler compound. The orthopedic device is then produced after the fastening elements have been fixed to the base layer and, if appropriate, after placement of further covering layers, in particular made of fiber-reinforced composite materials. The positioning device no longer needs to be coupled or connected to the fastening elements; instead the main body can be fed together with the fastening elements to the further necessary processing steps, for example cured at high temperatures and in a vacuum. The absence of the positioning device, which is preferably made of a metallic material, permits production that is free from differences in thermal elongation, such that more precise production of the orthopedic device can take place.

The abutment element and/or the mating piece can have bearing surfaces which are oriented obliquely or curved with respect to the pivot axis. By means of the oblique or curved bearing surfaces, it is possible to achieve stepless adaptation of the respective pivoting ranges or angle ranges through which the holders are pivotable about the pivot axis. If the abutment element is mounted displaceably, the oblique or curved bearing surfaces cause a force component to be exerted in the displacement direction in the event of a rotation of one holder relative to the other holder. If the first holder is pivoted to the maximum extent from the starting position, the abutment element is displaced by the mating piece of the first holder in the direction of the opposite mating piece and thereby limits the possible pivoting angle thereof, if appropriate to zero.

In a development of the invention, provision is made that the respective abutment element and the respective mating piece have correspondingly configured bearing surfaces oriented toward each other, in particular oriented in a wedge shape, such that, when an end position of the abutment element is reached, a basic position for the respective holder relative to the central piece is reached and defined, while for the other holder a maximum pivotability about the pivot axis in both pivoting directions is possible. When the abutment element is located in a central position, both holders are mounted pivotably in both directions about the pivot axis relative to the central piece. The angle range of the pivoting per holder is then accordingly halved. This is especially the case when about the abutment element has at mutually opposite ends in each case a wedge-shaped end region or an end region oriented toward each other, which is assigned to a respective correspondingly shaped mating piece. In a symmetrical embodiment of the abutment element, different pivoting ranges can be assigned to one holder or the other depending on the position of the abutment element.

The holders can be mounted on each other so as to be pivotable in an angle range of +−10° about the starting position, wherein the angle ranges can be different for each holder. Thus, one holder can have an angle range of +−10°, while the other holder has a pivoting and an angle range of +−5° about the starting position. This is defined by the design of abutment element and mating piece.

In a development of the invention, provision is made that the receiving devices for the fastening elements have, in the starting position of the holders, a longitudinal extent oriented parallel to each other. This ensures that, for example in joint devices, the fastening to the fastening elements can take place in an axially parallel manner, such that, in the production of the joint device, the bores, sleeves or receptacles can also be easily produced in an axially parallel manner.

In a system formed of a positioning device, as described above, and of a main body of an orthopedic device, provision is made that the main body, spanning a natural joint of a limb, is designed to bear integrally on the limb. The orthopedic device is preferably designed as an orthosis or prosthesis. If the main body is designed spanning a natural joint of a limb and bearing integrally on the limb, this also entails that a notional limb can be used in the case of a missing distal limb. The missing limb can then be modeled, for example by optical recording of a limb stump, processed in 3D simulation and then produced by a 3D printing method. After the fastening elements have been positioned on the main body and after the fastening elements have been fixed to the main body both on the proximal and also the distal side of the joint axis of a natural joint, production then takes place in common. During and after the production, the fastening elements maintain the positions, orientations and distances predefined by the positioning device. The main body can then be divided into a distal and a proximal component. In an embodiment as an orthosis, one then has a distal orthosis shell and a proximal orthosis shell; in a prosthesis one has a prosthesis socket, for receiving a stump, and a prosthesis component which is fixed to the prosthesis socket via a joint device or another fastening device which is secured to the fastening elements.

A receptacle for fixing the positioning device can be arranged on the main body. The receptacle can be a form-fit or force-fit receptacle. For example, a locking nut or a locking screw can be secured in the main body or on the main body in order to fix the positioning device there. Alternatively, this can be effected by a magnetic coupling. The receptacle can also be arranged on or in a support onto which the base layer of the main body is applied and formed. The receptacle does not have to be connected non-releasably to the base layer; a stable geometrical assignment is sufficient, with the fixing device oriented preferably along the joint axis, such that the pivot axis can be oriented orthogonally with respect to the joint axis.

The receptacle can be arranged in the region of the joint axis of the natural joint of the limb on which the orthopedic device, in particular the orthosis or prosthesis, can be arranged. If the longitudinal extent of the receptacle is coincident with the pivot axis of the holders, this can be easily realized by a plug connection or screw connection. The positioning device is then plugged onto the receptacle or screwed into the receptacle. In the case of a magnetic orientation, the orientation of the positioning device is effected via the orientation of the magnets and of the ferromagnetic elements as mating piece.

The main body can be molded on a model of the limb or on the limb itself and can have an inner contour corresponding to the contour of the limb. The respective fastening element is placed on the base layer of the main body, secured, optionally covered with one or more covering layers, and then finalized.

On the main body, a predetermined separation region or a predetermined separation point can be formed along which the main body can be divided into a proximal component and a distal component. The predetermined separation region can be formed by material weakening or by the omission of fiber composite material layers in this region. The predetermined separation region then contains only the base layer, which can also be composed of a plurality of layers of a fiber composite material.

BRIEF DESCRIPTION OF THE DRAWINGS

An illustrative embodiment of the invention is explained in more detail below with reference to the attached figures, in which: An illustrative embodiment of the invention is explained in more detail below with reference to the attached figures, in which.

DETAILED DESCRIPTION

Figure 1A:
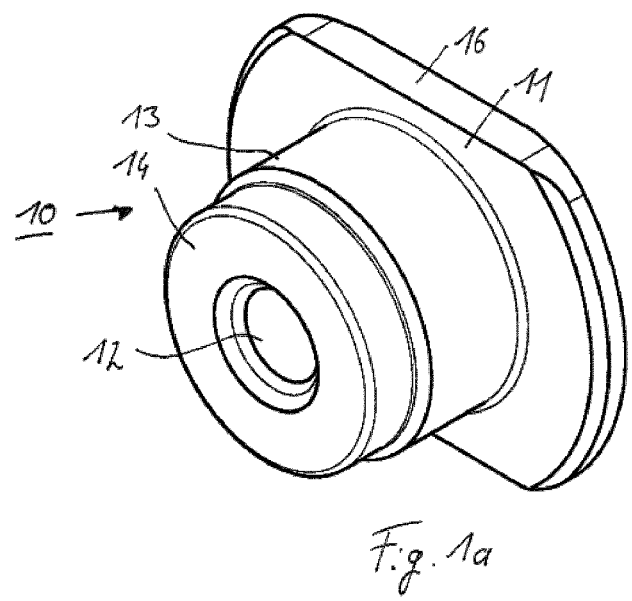
FIGS. 1a to 1d show views of a fastening element.
Figure 1B:
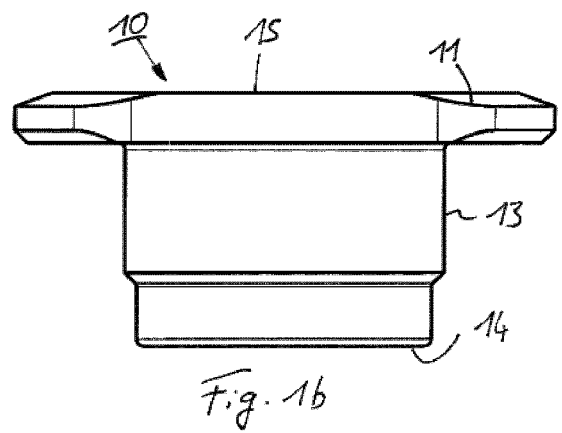
Figure 1C:
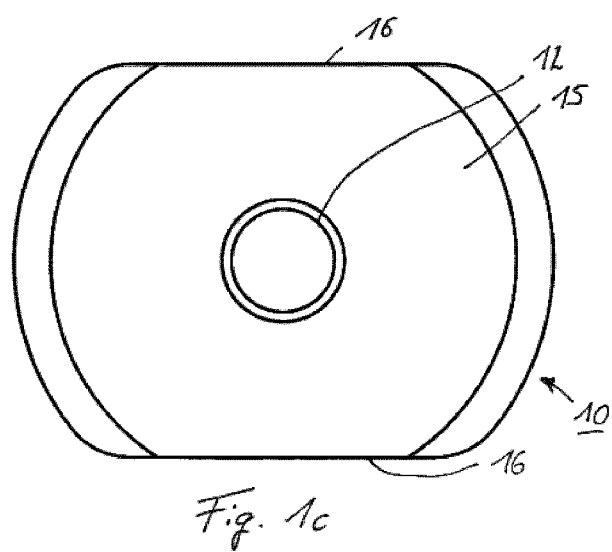
Figure 1D:
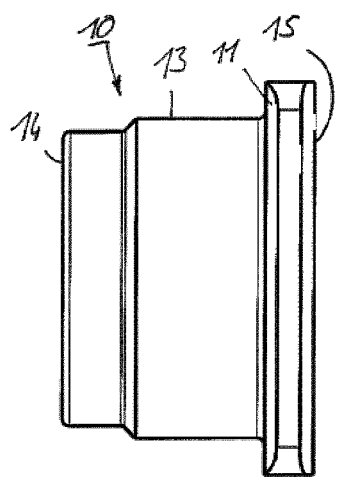

FIGS. 1a to 1d show different views of a fastening element 10, wherein FIG. 1a shows a perspective overall view, FIG. 1b shows a side view, FIG. 1c shows a bottom view, and FIG. 1d shows a further side view. The fastening element 10 has a base 11 which, in the illustrative embodiment shown, is substantially flat and plate-shaped. Bevels are formed at the edges of the base 11 in order to provide improved contact to a substrate or a support surface in order to form a smooth transition. In addition, connecting material or an adhesive can be arranged between the bevels and fiber composite materials in order to fix the fastening element 10 thereon. The base 11 is non-round and has two flattened regions 16 at mutually opposite sides. Between the flattened regions 16, the base 11 forms a radius, the continuation of which would lead to a circle shape. The contour of the base 11 thus corresponds to a circle with cut-off circle segments with parallel chords. A central bore with a form-fit element 12 in the form of an inner thread is formed in the middle of the base 11. The inner thread 12 extends along the longitudinal extent of a shaft 13, which protrudes from the base 11. A binding surface 14, which is substantially plane, is formed on the side of the shaft 13 remote from the base 11. Lying opposite the binding surface 14, a bottom surface 15 is formed on the base 11; the binding surface 11 and the bottom surface 15 are oriented substantially parallel to each other. The shaft 13 is rotationally symmetrical, and the central bore with the inner thread 12 is formed coaxially with respect to the longitudinal extent of the shaft 13. The shaft 13 is stepped in the front third directed toward the binding surface 10, that is to say the shaft 13 there has a smaller diameter than in the region of the base 11. The size of the shoulder can vary. In particular, the shoulder is chosen such that layers of a fiber composite material applied to the base 11 reach as far as this shoulder or at least do not reach beyond the shoulder in the direction of the binding surface. The outer contour of the shaft 13 can also have other outer contours, in particular a non-rotationally symmetrical outer contour in order to secure against rotation in addition to the securing against rotation provided by the non-round configuration of the base 11.

Recesses, projections or undercuts can also be arranged or formed on the fastening element 10, in order to provide further securing to a base layer for producing a main body for an orthopedic device. The use of the fastening element 10 in connection with the production of orthopedic devices such as orthoses, prostheses or other orthopedic components is explained below. The base 11 serves to secure the fastening element 10 on a main body, while the form-fit element 12 serves to ensure that further components of an orthopedic device can be secured to the fastening element 10, for example joints, actuators, dampers or other devices or components.

The production of an orthosis as an orthopedic device is explained in more detail with reference to FIGS. 2 to 4.

Figure 2:
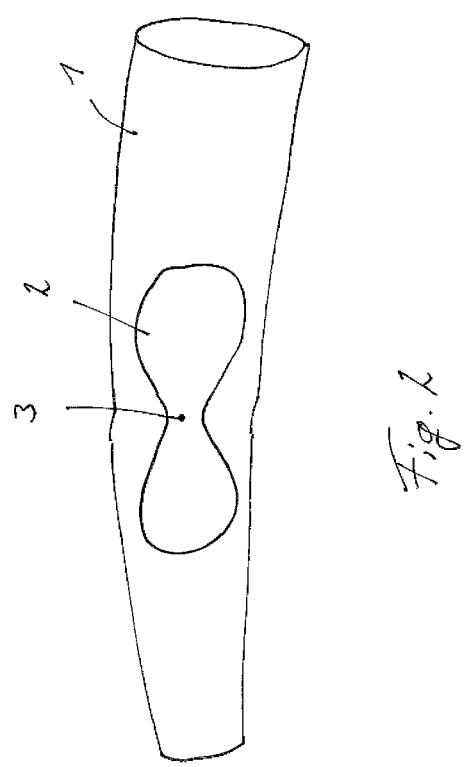
FIG. 2 shows a schematic perspective view of a support with an applied base layer.

FIG. 2 shows a schematic view of a support 1 which is shaped corresponding to the body part on which an orthosis or prosthesis is intended to be worn. In the illustrative embodiment shown, the support 1 is formed as a part of a leg with a thigh portion, a knee joint and a lower leg portion. As an alternative to an embodiment in the form of a leg, the support can also be configured in the form of an arm or part of an arm. It is also possible to configure the support 1 in any other form that is required in order to form an orthosis. If a prosthesis is to be produced, the support 1 can correspond only partially to the shape of the body of the patient or prosthesis user, i.e. where the stump is still present. The distal part of the support is then modeled, for example using a 3D computer method or in some other way.

A base layer 2, which is formed from one or more blanks, is applied to the support 1. The base layer 2 is preferably formed from a fiber composite material, for example from a prepreg or from another fiber composite material. In the illustrative embodiment shown, the base layer 2 is formed in one piece and extends over a joint axis 3 of a natural or assumed joint of the respective limb. In the illustrative embodiment shown with the support 1 as a thigh part, the base layer 2 covers the knee-joint axis 3. The base layer 2 is sufficiently flexible to be able to conform to the surface structure of the support 1. The support 1 can be modified according to the actual contour of the limb, for example by addition of material, smoothing of a 3D model or the like, for example in order to be able to arrange padding elements on the inner face of the orthosis or prosthesis that is to be produced. In the case of a prosthesis, it may be necessary for the prosthesis socket or the receiving device to be chosen larger, so as to be able to receive liners or other protective coverings without exerting too great a pressure on the body part.

The base layer 2 is of a closed configuration, i.e. not open for the passage of components such as fastening elements 10 that are applied to the base layer 2. The base layer 2 can be fixed to the support 1 either mechanically or by an adhesive. The fixing is done in such a way that the base layer 2 is removable again after the orthosis or prosthesis has been produced.

Figure 3:
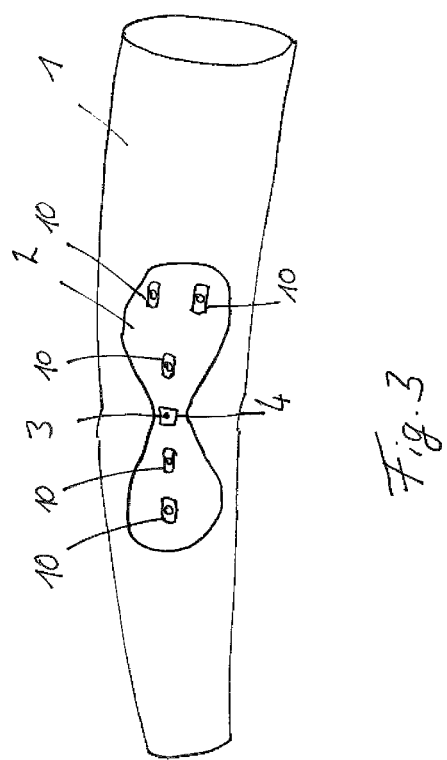
FIG. 3 shows a base layer according to FIG. 2 with attached fastening elements.
Figure 4:
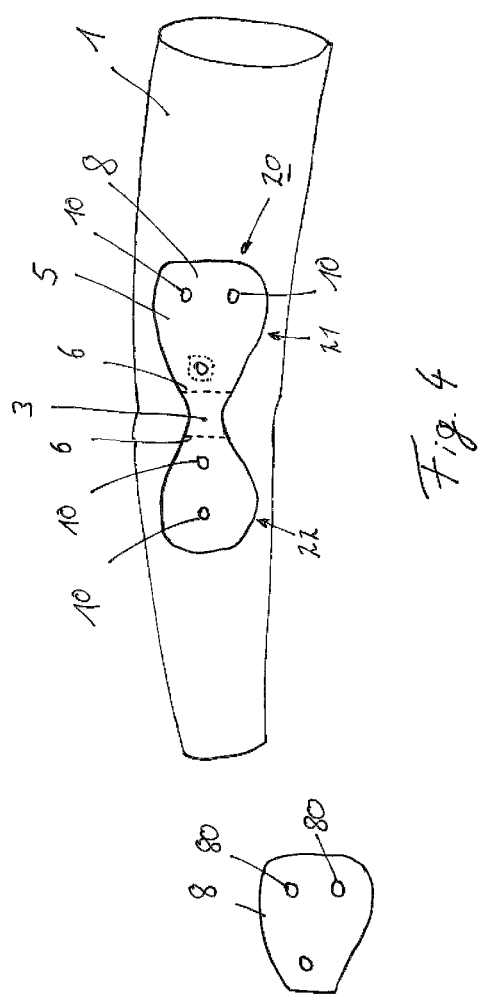
FIG. 4 shows a schematic side view with an applied fiber composite material layer.

FIG. 3 shows a next phase in the production of the orthosis components, in which phase fastening elements 10, as have already been described with reference to FIG. 1, are placed on the lateral surface of the base layer 2, i.e. on the surface facing away from the support 1. The fastening elements 10 are applied via the underside 15, i.e. the surface of the base 11 facing away from the bearing surface 14 The fastening elements 10, in the illustrative embodiment five fastening elements 10, of which two are positioned in the distal region and three in the proximal region, are positioned on the base layer 2 preferably via a positioning device. The positioning device is explained in more detail further below. By means of the positioning device, the fastening elements 10 are arranged on the base layer 2 at defined spacings from each other and from the joint axis 3. The positioning device is secured to or placed on a receptacle 4, for example plugged on, screwed on or fixed via a magnetic lock. The receptacle 4 is preferably already arranged on the support 1 and protrudes through a recess in the blank of the base layer 2. The receptacle 4 can be worked into the support 1, for example cast in or inserted. It preferably has a thread, a sleeve or a peg, of which the longitudinal extent coincides with the knee-joint axis. Generally speaking, the longitudinal extent of the receptacle 4 should coincide with the joint axis about which an orthosis upper part pivots relative to an orthosis lower part or a proximal component pivots relative to the distal component of the orthosis.

The fastening elements 10 are fixed on the base layer 2, for example by an adhesive, a filler compound, or by using a compensating material. The aim is that the fastening agent, such as filler or adhesive, does not deform during the subsequent processing of the orthosis. To produce the orthosis, the latter can be cured at high temperatures and under vacuum, which must not cause displacement of the fastening elements 10 or tilting of the fastening elements 10.

After all of the fastening elements 10 are fastened on the base layer 2, the positioning device is removed, as will be explained later. The fastening elements 10 and also the receiving device 4 remain securely on the outer or lateral surface of the base layer 2.

At least one layer 8 of a fiber composite material with punched-out recesses is then placed over the shafts of the fastening elements 10, wherein the recesses in the layer 8 of a fiber composite material are dimensioned such that the respective shaft can pass through, but not the base 11. In this way, the base 11 of the fastening element 10 is embedded between the base layer and an outer composite fiber material layer 8. Predetermined separation lines 6, along which separation can take place easily or more easily, can be worked into the outer fiber composite material layer 8. In the illustrative embodiment shown, two predetermined separation lines 6 form a predetermined separation region in which the joint axis 3 and also the receiving device 4 lies before the anchor plate. After the separation at the predetermined separation lines 6, a proximal component 21 and a distal component 22 of the orthosis are obtained, i.e. a thigh shell 21 and a lower-leg shell 22, with fastening elements 10 laminated therein. The separation or removal of the predetermined separation region between the predetermined separation lines 6 is effected only after the base layer 2 together with the at least one fiber composite material layer 8 has been bonded to the outside and then secured on top of each other. This takes place, for example after application of an underpressure, in an oven at elevated temperatures. The fiber composite material layers 8 are preferably applied as far as the shoulder in the shaft 13. The shoulder ensures that a sufficient material thickness is present in the region of the fastening elements. A fiber composite material layer 8 as blank with pre-formed recesses 80, which correspond in terms of diameter to the shaft diameters of the shafts 13 and in terms of their positions to the positions of the fastening elements 10 on the base layer 2, are shown on the left in FIG. 4.

After the laminate material has cured and cooled, a main body 20 is present with a continuous base layer 2 on the inner side, fastening elements 10 placed thereon, and at least one layer, preferably several layers, of fiber composite material 8 which are connected to each other such that the fastening elements 10 are laminated in. After curing and cooling, the orthosis main body 20 is separated, for example sawn through, in the region of the predetermined separation points 6, in order to separate the thigh shell or proximal orthosis component 21 from the lower-leg shell or distal orthosis component 22. The orthosis components 21, 22 are then removed from the support 1, optionally re-worked and ground, provided with receptacles for fastening devices such as straps, and equipped with the necessary attachments such as joint devices, dampers or pads.

Figure 5:
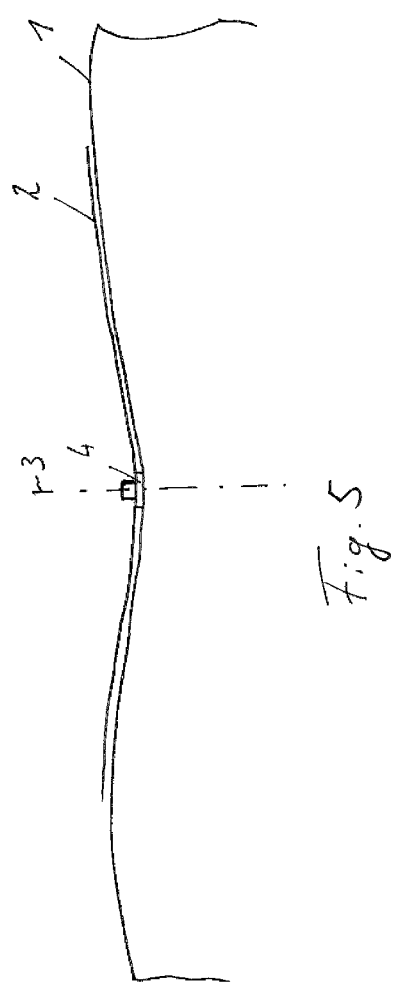
FIG. 5 shows a sectional view according to FIG. 2.
Figure 6:
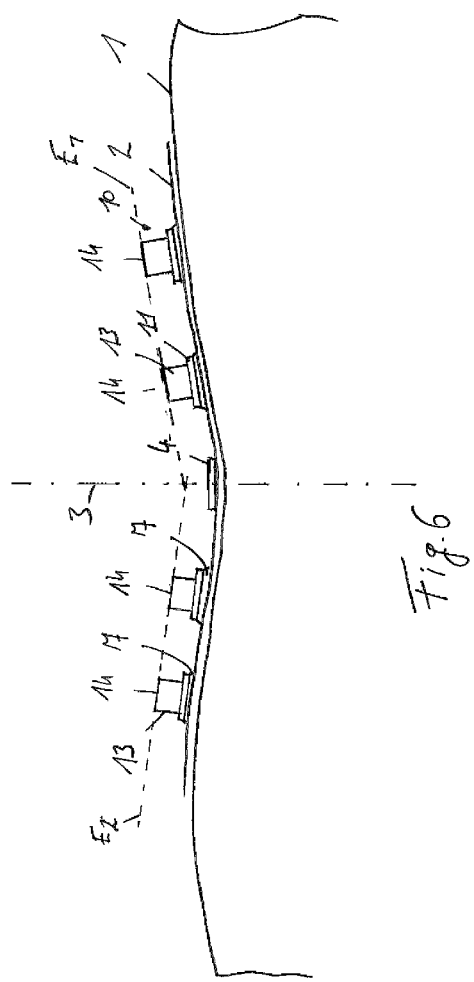
FIG. 6 shows a sectional view according to FIG. 3.
Figure 7:
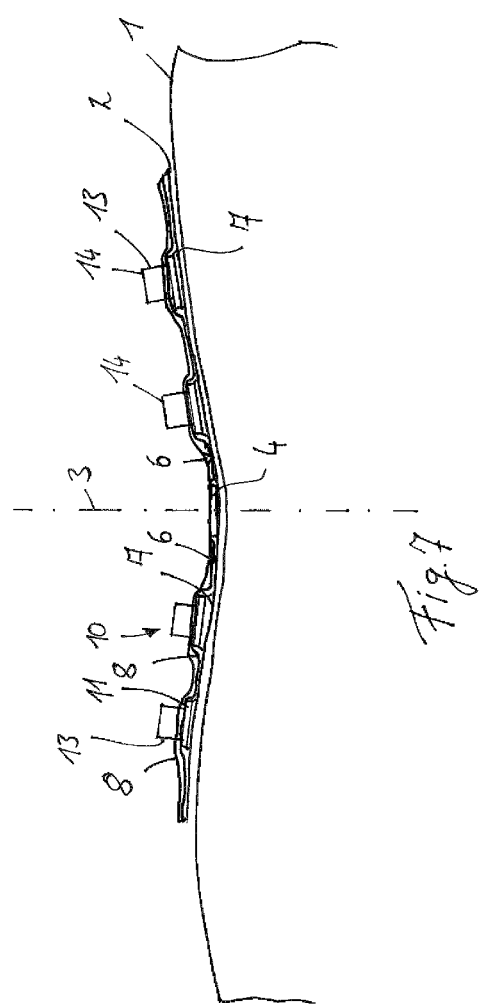
FIG. 7 shows a sectional view according to FIG. 4.

FIGS. 5 to 7 show the production sequence in a schematic sectional view. First, the anchor plate or the receptacle 4 is positioned on the support 1, specifically in the region of the joint axis of the natural joint or of a compromise axis 3. The base layer 2 is then applied to the outer or lateral surface of the support 1 and optionally fixed. The material of the base layer 2 can be plastically deformable and have low restoring forces, so as to allow it to bear as fully as possible on the outer surface of the support 1. The spacing from the support 1 is indicated in order to make matters clearer.

FIG. 6 shows the state after the fastening elements 10 are applied to the lateral surface of the base layer 2. The fastening elements 10 are positioned on the base layer 2, in a manner aligned with the joint axis 3, via a positioning device. It will be seen that the respective bases 11 of the fastening elements 10 should be arranged as close as possible to the surface of the base layer 2. In the illustrative embodiment shown, the connection of the respective underside 15 of the respective base 11 of the fastening elements 10 is effected via a filler compound 7, which at the same time evens out irregularities in the surface of the base layer 2 and ensures that the fastening elements 10 are rigidly anchored on the base layer 2.

It will be seen from FIG. 6 that all of the binding surfaces 14 lie in a respective plane E1, E2, wherein the plane E1 stands for the fastening elements 10 of the proximal component 21 and the plane E2 stands for the fastening elements of the distal component 22. It will be seen from FIG. 6 that the planes E1, E2 in the illustrative embodiment shown do not lie parallel to each other or form a common plane. This would be the case if for example, in the illustrative embodiment, there was a completely straight leg on the lateral side or medial side. A more natural depiction is shown in which there is a lateral curvature both of the thigh and of the lower leg starting from the knee joint. In the illustrative embodiment shown, both planes E1, E2 intersect each other in the joint axis 3, thus resulting in a common section line, which is preferably orthogonal to the joint axis 3. It is also possible that the binding surfaces do not lie exactly in a plane E1, E2, and instead there is a certain vertical offset. It is likewise possible that the planes E1, E2 do not intersect each other in the joint axis 3, for example because a vertical offset has been established. All the binding surfaces 14 of all the fastening elements 10 of an orthosis component 21, 22 preferably lie on a common plane E1, E2. The longitudinal extents of all the bores, pegs or form-fit elements 12 such as inner threads or outer threads in the fastening elements 10 are preferably oriented parallel to each other, in each case with respect to an orthosis component. That is to say, all the longitudinal axes of the fastening elements 10 on the proximal orthosis component 21 are preferably oriented parallel to each other, likewise the longitudinal extents or longitudinal axes of the fastening elements 10 on a distal orthosis component 22.

After the fastening elements 10 have been secured on the base layer 2, several layers 8 of a composite fiber material are applied, as shown in FIG. 7, for example resin-impregnated fiber mats, optionally with addition of further adhesives, hardeners, solvents or the like. The layers 8 of the fiber composite material or of the fiber composite materials can be applied in different orientations, in order to laminate in the bases 11 of the fastening elements 10. For this purpose, recesses 80 or punched holes corresponding to the shape and the diameter of the respective shafts 13 are formed in the blanks of the fiber composite material layers 8. Since the bases 11 are greater than the diameters of the shafts 13, no fastening element 10 can be removed from the respective orthosis component 21, 22 after the fiber composite material layers 8 have been connected to the base layer 2. On account of the non-round configuration of the base 11, all of the fastening elements 10 are secured against rotation. To increase the securing against rotation, it is possible for projections, hooks, undercuts or the like to be provided, so that the fastening elements 10 cannot rotate after the orthosis components 21, 22 have been produced.

The binding surfaces 14 are not all covered by a fiber composite material layer 8, so as to ensure accessibility to the form-fit elements 12 and to ensure a defined bearing of the components that are to be mounted. In order to avoid contamination of the form-fit element 12, it can be secured In the embodiment according to FIG. 1, in which the form-fit element 12 is designed as an inner thread, this can be achieved for example by a screw which is unscrewed after the orthosis component has been produced. If the form-fit element 12 is designed as an outer thread, a screw cap can be screwed on in order to protect the thread. The same applies to other form-fit elements such as pegs, bores or the like. After the fiber composite material layers 8 have been applied, the orthosis main body 20 is produced on the support 1 under vacuum and at elevated temperatures. The predetermined separation points 6 are formed proximally and distally at the joint axis 3, for example by impressions or cuts made in the fiber composite material layers 8 or simply by applying no or fewer fiber composite material layers 8 in the region between the predetermined separation points 6.

After curing and separation of the orthosis components 21, 22 from each other, other components can be secured to the fastening elements 10.

Figure 8:
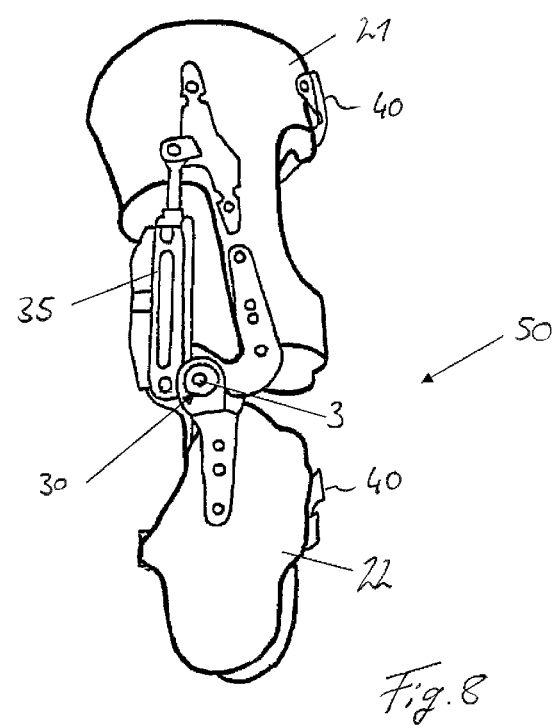
FIG. 8 shows a view of a finished orthosis.

FIG. 8 shows a variant of a knee-joint orthosis in which the proximal component 21 is designed as a thigh shell and the distal component 22 as a lower-leg shell. Fastening devices 40, which are designed as straps, are arranged on both orthosis components 21, 22 in order to secure the orthosis 50 to a leg. A joint device 30 with a hydraulic actuator 35 is secured to the no longer visible fastening elements, for example via screws The joint device 30 has its pivot axis in the region of the joint axis 3 of the natural joint. The position of the joint axis 3 on the joint device 30 is made safe by the exact positioning of the fastening elements relative to the joint axis 3 of the natural joint via a positioning device. The design of the orthosis components 21, 22 in the form of the orthosis shells is adapted very effectively and individually to the shape of the respective orthosis user. The production of the orthosis can take place without previously arranging the joint device 30 or a hydraulic component 35 on the orthosis components 21, 22, which is extremely advantageous in respect of the high temperatures and negative pressures arising during manufacture, in particular for electronic controls. The nature of the manufacturing prevents any limit on the attachment parts that are to be used, such as dampers, controls or the like.

Figure 9:
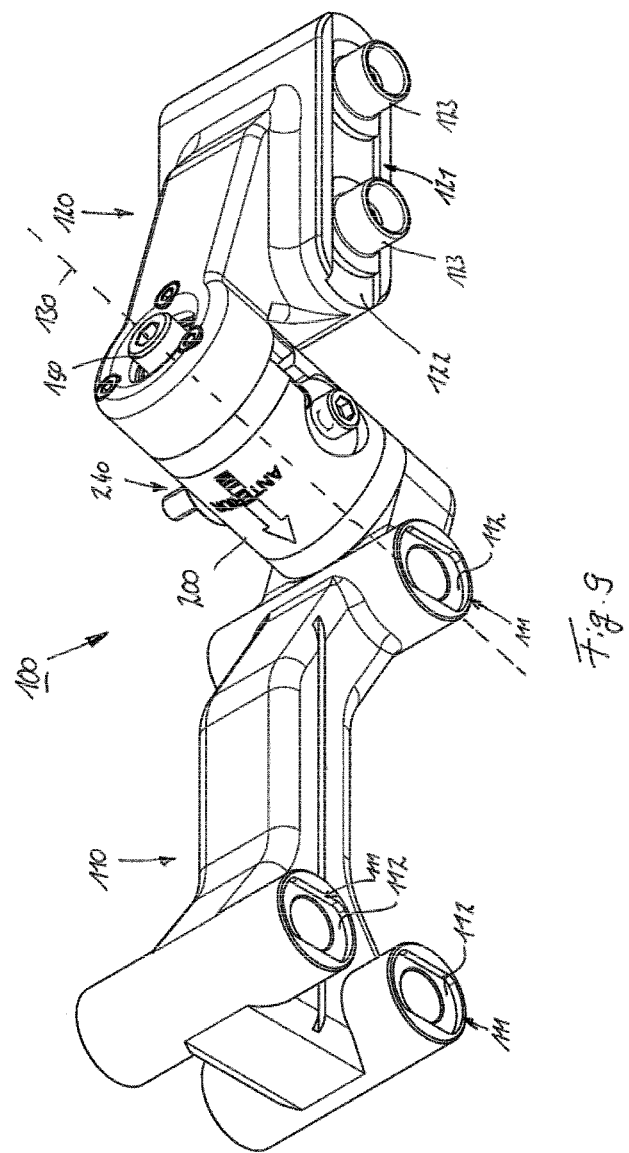
FIG. 9 shows a positioning device for the fastening elements.

FIG. 9 shows a perspective view of a positioning device 100 for positioning and aligning fastening elements 10 (not shown), which are of the kind explained for example with reference to FIG. 1. The positioning device 100 has a central body 200 on which two holders 110, 120 are arranged pivotably about a pivot axis 130. In the illustrative embodiment shown, a first holder 110 is provided for assigning and arranging the fastening elements 10 on the proximal orthosis component 21, while the second holder 120 is provided for the fastening elements 10 on the distal orthosis component 22. Both holders 110, 120 have receiving devices 111, 121, which are designed as sleeves with through-bores through which fixing elements 123 can be guided. In FIG. 9, the fixing elements 123 are shown only on the second holder 120. On the receiving devices 111, 121, bearing surfaces 112, 122 are formed for the upper face of the base 11 of the fastening elements 10. The upper face of the base 11 is the side of the base 11 lying opposite the underside 15. In the illustrative embodiment shown, all the bearing surfaces 112, 120 are arranged on a common holder 110, 120 in a common plane, in order to ensure that all of the fastening elements 10 lie in a common plane when they are arranged on the respective holder 110, 120 and are secured there by the fixing elements 123.

Arranged on the central body 200 is a fixing device 240 in the form of a screw via which the central body 200 is secured to the receptacle 4 which is fixed on the support 1 or the base layer 2. The longitudinal extent of the fixing device 240 runs perpendicular to the pivot axis 130 and preferably intersects the latter, such that the longitudinal axis of the fixing device 240 is orthogonal to the pivot axis 130. The longitudinal extent of the fixing device 240 is preferably flush with the longitudinal axis 3 of the joint device and of the natural joint axis or the compromise axis for the natural joint. When all of the bearing surfaces 112, 122 are located in parallel planes or in a common plane, depending on how the planes of the bearing surfaces 112, 120 are arranged, the positioning device 100 is located in a starting position. From this starting position, both the first holder 110 and the second holder 120 can be pivoted through a limited angle range, for example +/−10°, about the pivot axis 130. Joint devices 30 or also other attachment parts may be sensitive in respect of a possible angular offset of their binding sites. By means of the positioning device 100 it is possible, besides the exact positioning of the fastening elements 10 relative to each other and to a joint axis 3 about a joint device 30, to take account of this maximum angular offset. There is the possibility of fixing the extent of the angular offset of the two holders 110, 120 in advance. For example, if a maximum offset of the planes of the binding surfaces 14 of 10° is admissible, this maximum angle range can be set with the positioning device 100. If, proceeding from the starting position, the first holder 110 is then applied to the base layer 2 and requires a pivoting in the lateral direction through 3°, proceeding from the starting position, a maximum pivoting range of a further 7° in the lateral direction is available for the second holder 120. If, with such a maximum setting, a satisfactory orientation of the undersides 15 of the bases 11 of all the fastening elements 10 is not possible, the whole positioning device 100 has to be offset further laterally, or the fastening elements 10 have to be secured to the base layer via a compensating compound or a filler compound.

Figure 10:
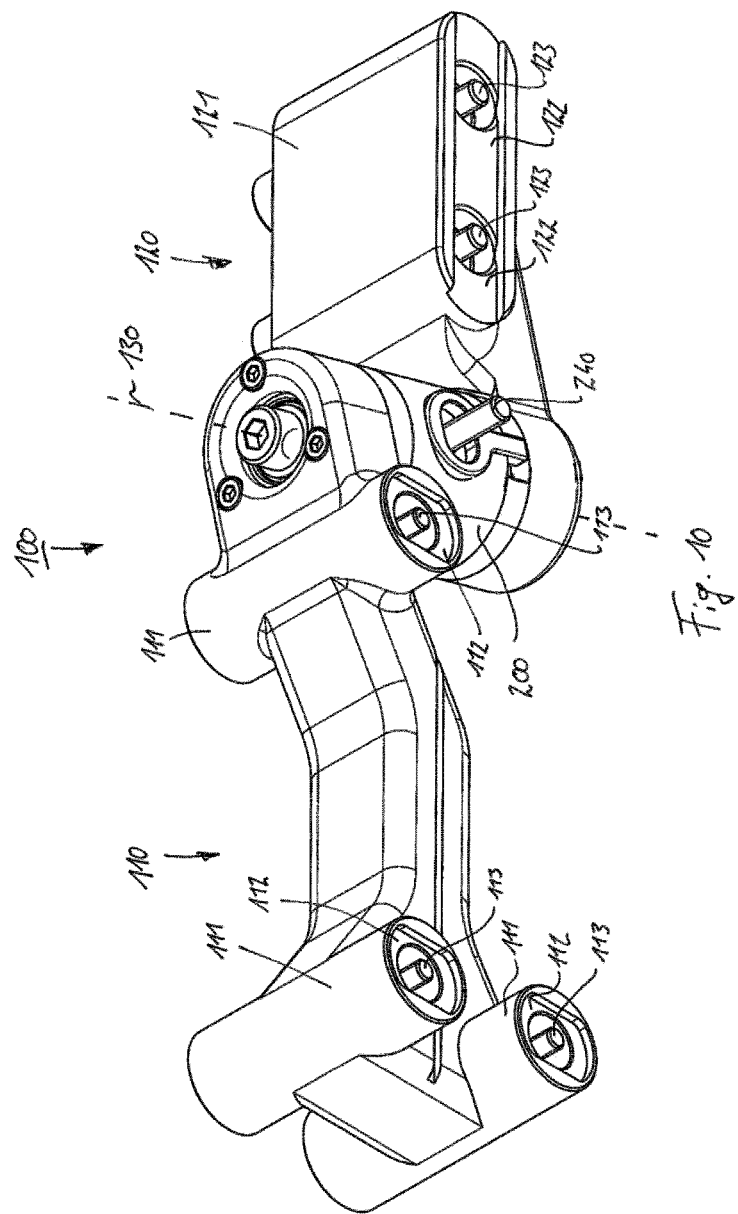
FIG. 10 shows the positioning device according to FIG. 9 in a bottom view.

The positioning device 100 is designed with axial symmetry. FIG. 9 shows an upper face, for example, while FIG. 10 shows the underside. A comparison of FIGS. 9 and 10 shows that identical receptacles for the fastening elements 10 are formed on both sides of the receiving devices 111, 112. The fixing device 240 can be removed from the central body 200 and re-inserted the other way round, such that the positioning device 100 is suitable both for a right leg and for a left leg and also for medial and also lateral positioning on base layers 2.

In FIG. 10, the fixing elements 113 in the form of screws are shown in all of the receiving devices 111. The inner threads 12 according to FIG. 1 are designed corresponding to outer threads on the fixing elements 113, so that assembly proceeds in such a way that, in each receiving device 11, the shaft 13 is inserted with the binding surfaces in front into the bores of the sleeve-like receiving devices 111. The fastening elements are fixed via the fixing elements 113. It will be seen that the shape of the bearing surfaces 112 of the receiving device 111 corresponds to the shape and contour of the bases 11, such that each fastening element is assigned and oriented in a defined manner on the respective holder 110, 120. A groove-like guide for the two bases 11 of the two fastening elements 10 is provided in the second holder 120. Further insert elements such as rails or strengthening elements or spacers can be received therein, which elements can likewise be laminated in place. After the fastening elements 10 have been fixed inside the receiving devices 111, 121, the positioning device 100 is secured with the fixing device 240 in the receptacle 4. A central screw 150 along the pivot axis 130 keeps the two holders 110, 120 in a defined position relative to each other, preferably in the starting position in which all of the undersides 15 of the fastening elements 10 are oriented relative to each other in a common plane or at least in parallel planes. When the fixing by the central screw 150 is released, the two holders 110, 120 are able to pivot about the pivot axis 130 within the predefined angle range.

Figure 11:
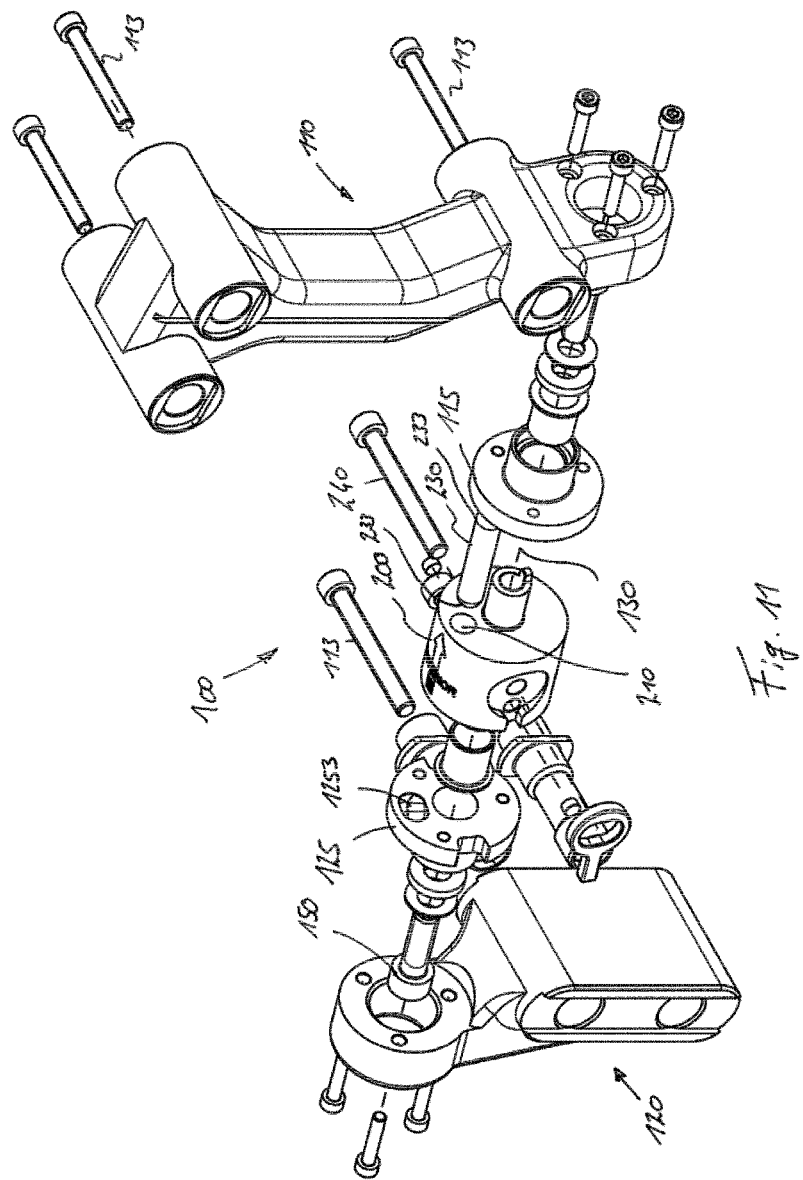
FIG. 11 shows an exploded view of the positioning device.

FIG. 11 shows an exploded view of the positioning device 100 with the central body 200, and the fixing device 240 which is guided through a bore inside the central body 200 and orthogonally intersects the pivot axis 130. The fixing elements 113 can be seen, likewise the two holders 110, 120 and the central screw 150, which extends along the pivot axis 130. Inside the central body 200, an abutment element 230 is likewise mounted longitudinally displaceably in a bore 210 in the central body 200. The bore 210 extends parallel to the pivot axis 130.

Mating pieces 115, 120 with bearing surfaces 1153, 1253, which interact with the bearing surfaces 233 at the two ends of the abutment element 230, are arranged on the holders 110, 120 via three screws. The interaction is explained below. In the illustrative embodiment shown, the mating pieces 115, 125 are mounted in a fixed position on the respective holder 110, 120. There is also the possibility, for example by means of oblong holes, to permit a rotatability of the mating pieces 115, 125 on the respective holder 110, 120. The angle range can be set via the rotation of the mating pieces 115, 125; the maximum angle range can be increased, for example, by exchanging the mating pieces 115, 125. It is likewise possible, for example by means of adjustment screws, to modify the position of the abutment surfaces 1153, 1253 in order to set the angle range about which the first holder 110 can be pivoted relative to the second holder 120 about the pivot axis 130. For this purpose, adjustment screws can be screwed into or out of the recesses in the mating piece 115, 125.

Figure 12:
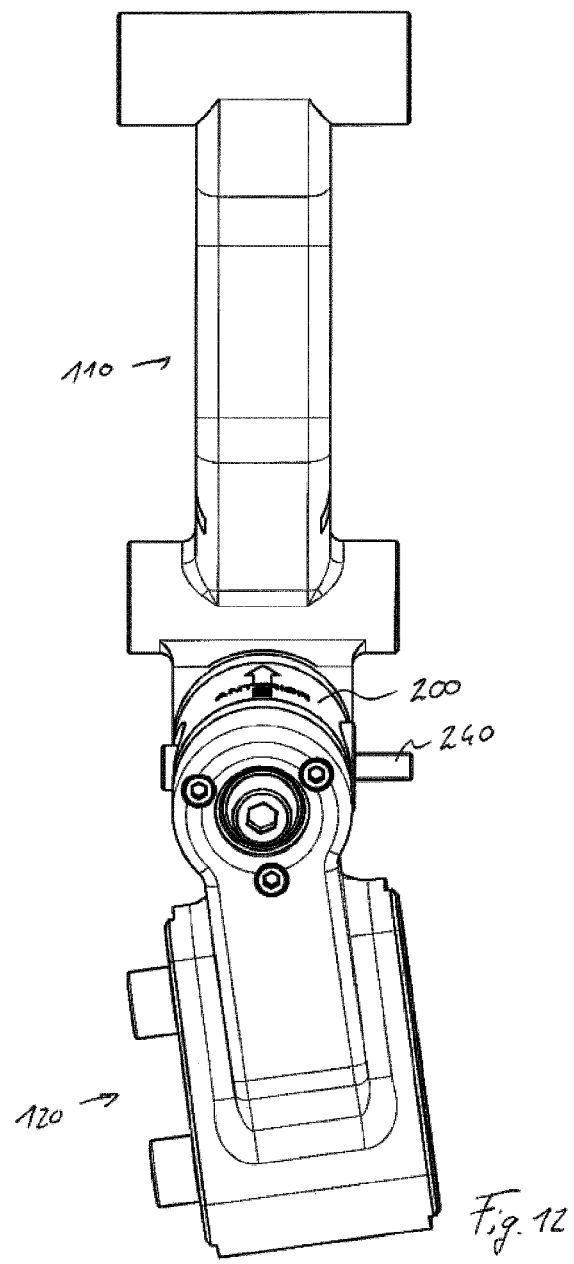
FIGS. 12 and 13 show views of holders at different angle positions.
Figure 13:
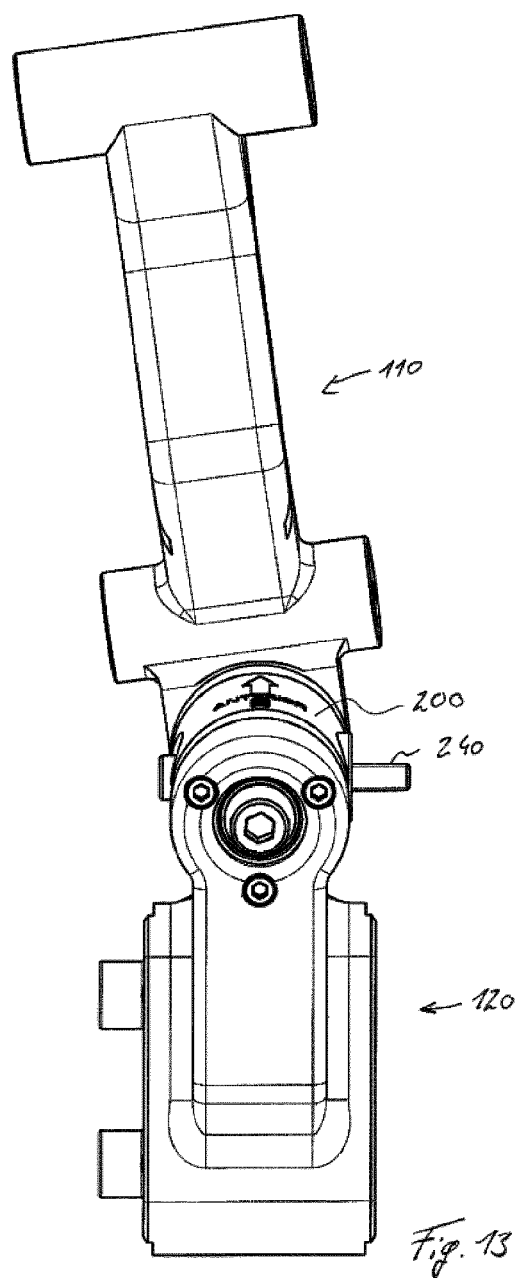

FIGS. 12 and 13 show the positioning device 100 in the same view. In FIG. 12, proceeding from the starting position, the second holder 120 is pivoted counterclockwise about the pivot axis 130 to a maximum extent. In FIG. 13, proceeding from the starting position, the first holder 110 is pivoted counterclockwise to a maximum extent. The maximum pivoting range is reached in both positions in FIGS. 12 and 13. Sectional views corresponding to FIGS. 12 and 13 are shown in FIGS. 14 and 15.

Figure 14:
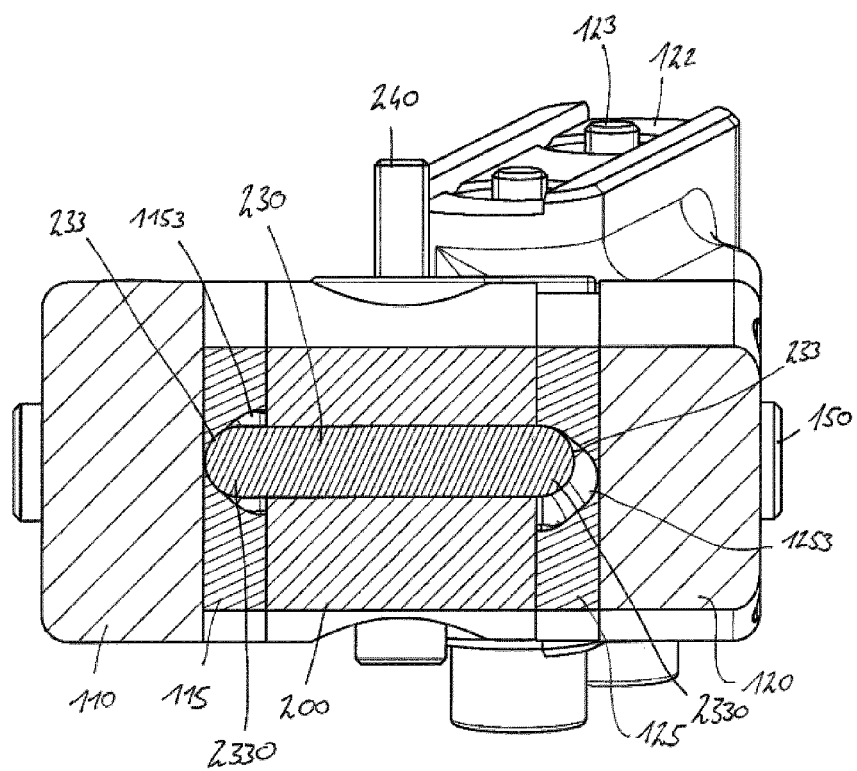
FIGS. 14 and 15 show sectional views of FIGS. 12 and 13.

FIG. 14 shows a section through the central piece 200 in the region of the abutment element 230. In the sectional view, the abutment element 230 looks like a feather key, which is arranged displaceably inside the central piece 200. In FIG. 14, a rounded end region 2330 with corresponding bearing surfaces 233 is in abutment with a correspondingly shaped bearing surface 1153 in a recess in the mating piece 115. The mating piece 115 is connected rigidly to the first holder 110 in terms of rotation. The mating piece 115 is located in the starting position, in which the first holder 110 is correspondingly oriented. In this starting position, the abutment element 230 can be displaced to the maximum extent to the left parallel to the pivot axis 130. In this way, the right-hand end of the abutment element 230 is brought out of the free space inside the mating piece 125 of the second holder 120, such that the second holder 120 can move to the maximum extent in both directions. In the illustrative embodiment shown, the holder 120 was pivoted upward about the pivot axis, such that the bearing surface 1253 bears on the rounded bearing surface 233 of the right-hand end of the abutment element 230. If both holders 110, 120 were located in the starting position and the abutment piece 230 were located in the middle, both holders 110, 120 would be able to pivot about the pivot axis 130 by the same angle until the bearing surfaces 233, 1153, 1253 came to bear on each other. The further the abutment element 230 is displaced in one direction or the other, the more the possible pivoting range of the other holder increases or decreases in the one pivoting direction or the other. If the bearing surfaces 1153, 1253 of the mating pieces 115, 125 are not of the same shape or symmetrical, different angle adjustment possibilities arise. In addition to a rounded shape of the bearing surfaces 233, 1153, 1253, the latter can also have other shapes.

Figure 15:
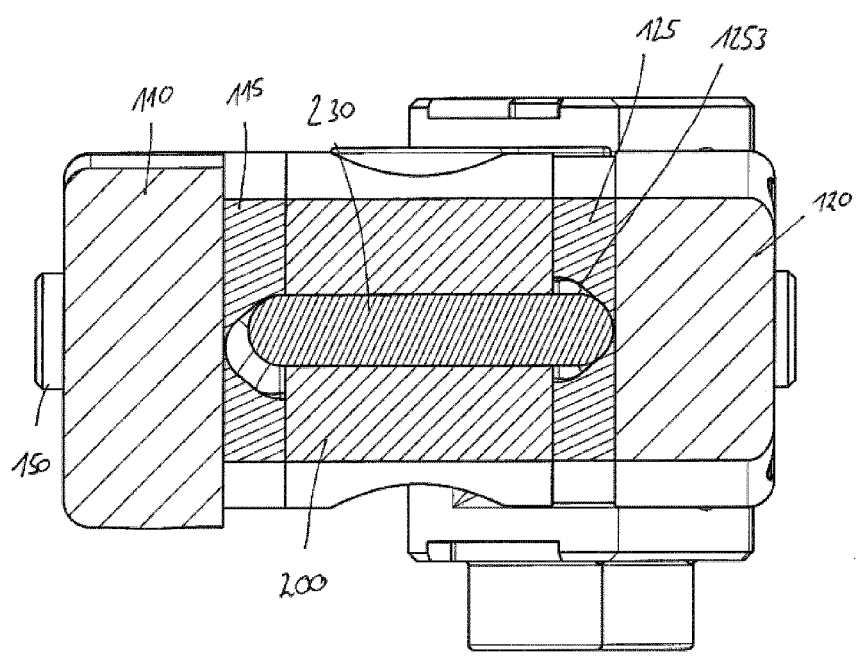

FIG. 15 shows the reverse position according to FIG. 13: the abutment element 230 has been displaced to the maximum extent to the right, as a result of which the right-hand end of the abutment element 230 lies in the recess in the mating piece 125 and thus abuts the bearing surfaces 1253. This results in a maximum pivotability of the first holder 115 about the pivot axis 130.

Figure 16:
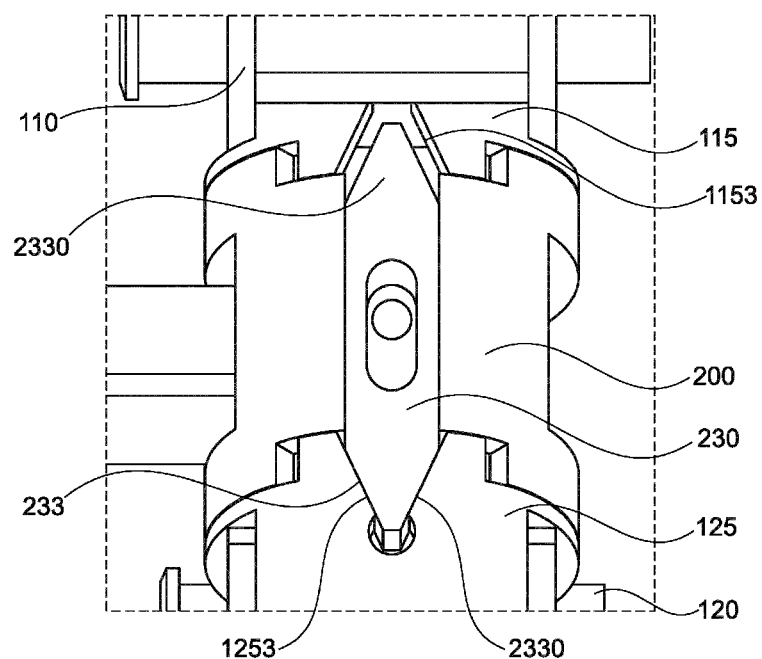
FIG. 16 shows a variant of the central piece.

An alternative embodiment of the abutment element 230 is shown in FIG. 16 in which, instead of a rounded configuration of the two end pieces 2330, a straight, conical configuration of the end pieces 2330 and of the bearing surfaces 233 is present. A corresponding conical configuration of the bearing surfaces 1153, 1253 permits a large bearing surface and therefore low surface pressure. The longitudinal displaceability of the abutment element 230 permits a simple adjustment. In the abutment element 230, an oblong hole can be formed through which a screw or a movement limiter can be inserted in order to limit the adjustment range of the holders 110, 120 relative to each other. The abutment element 230 can be fixed in the respectively desired position. The oblique configuration of the bearing surfaces 233, 1153, 1253 imposes a displacement of the abutment element 230 upon contact along the displacement direction toward the opposite holder, as a result of which the adjustment angle thereof in both pivoting directions changes. The respective pivoting range of the holders can be modified within a predefined angle range according to the positions of the holders relative to each other. Provision is made that the holders 110, 120 are held securely in the respectively found optimal position in which the fastening elements 10 are placed onto the base layer 2. This can be done, for example, by clamping by the central screw 115.

I claim:

1. A positioning device for arranging and orienting a plurality of fastening elements on a base layer of a main body of an orthopedic device, the positioning device comprising:
 a first holder having at least one receiving device for a fastening element; and
 a second holder having at least one receiving device for a fastening element;
 a central piece defining a pivot axis; and
 a central screw extending along the pivot axis;
 wherein the first holder and the second holder are mounted on each other so as to be pivotable about the pivot axis about a limited angle range proceeding from a starting position, wherein the holders are mounted pivotably on the central piece, wherein a fixing device for orientation of the positioning device on the main body is arranged in or on the central piece, wherein the first holder and the second holder are individually and independently pivotable about the central piece, wherein the first holder and the second holder are independently fixed and oriented on the central piece, and wherein the central screw clamps the first holder and the second holder in a defined position relative to each other.

2. The positioning device as claimed in claim 1, wherein an abutment element is arranged on the central piece and, with a mating piece arranged on the respective first or second holder, limits the angle range.

3. The positioning device as claimed in claim 2, wherein at least one of the abutment element and the mating piece has bearing surfaces oriented obliquely or curved with respect to the pivot axis.

4. The positioning device as claimed in claim 3, wherein the abutment element and the respective mating piece have correspondingly configured bearing surfaces oriented toward each other.

5. The positioning device as claimed in claim 2, wherein at least one of the abutment element and the mating piece are arranged adjustably on the central piece or the first or second holder.

6. The positioning device as claimed in claim 2, wherein the abutment element is arranged on the central piece in such a way as to be displaceable and securable along the pivot axis.

7. The positioning device as claimed in claim 2, wherein the abutment element has, at mutually opposite ends, a respective wedge-shaped end region, to which a correspondingly shaped mating piece is assigned.

8. A system comprised of a positioning device as claimed in claim 1 and a main body of an orthosis or prosthesis, wherein the main body, spanning a natural joint of a limb, is designed to bear integrally on the limb.

9. The system as claimed in claim 8, wherein a receptacle for fixing the positioning device is arranged on the main body.

10. The system as claimed in claim 9, wherein the receptacle is arranged in the region of a joint axis of the natural joint of the limb on which the orthosis or prosthesis can be arranged.

11. The system as claimed in claim 8, wherein the main body is molded on a model of the limb or on the limb itself and has an inner contour corresponding to the outer contour of the limb.

12. The system as claimed in claim 8, wherein a predetermined separation region or at least one predetermined separation point is formed on the main body, where the main body can be divided into a proximal and a distal orthosis component or prosthesis component.

13. The positioning device as claimed in claim 1, wherein each holder has a plurality of receiving devices that each receive one fastening element.

14. The positioning device as claimed in claim 13, wherein the plurality of receiving devices have bearing surfaces for the respective fastening element, which bearing surfaces lie on the first or second holder in a common plane.

15. The positioning device as claimed in claim 1, wherein the receiving devices are configured as sleeves.

16. The positioning device as claimed in claim 1, wherein the fixing device orients the pivot axis orthogonally with respect to a joint axis of a joint device that can be arranged on the main body.

17. The positioning device as claimed in claim 1, wherein the holders are mounted on each other so as to be pivotable within an angle range of +/−10° about the starting position.

18. The positioning device as claimed in claim 1, wherein the at least one receiving device of the first holder and the at least one receiving device of the second holder, in the starting position, have a longitudinal extent oriented parallel to each other.

* * * * *